United States Patent
Gerion et al.

(10) Patent No.: US 8,426,152 B2
(45) Date of Patent: Apr. 23, 2013

(54) ENZYMATIC ASSAY FOR LSPR

(75) Inventors: Daniele Gerion, Albany, CA (US); Randy Storer, Bulingame, CA (US); Hiroyuki Takei, Hatoyama (JP)

(73) Assignee: LamdaGen Corporation, Burlingame, CA (US)

( * ) Notice: Subject to any disclaimer, the term of this patent is extended or adjusted under 35 U.S.C. 154(b) by 739 days.

(21) Appl. No.: 11/966,436

(22) Filed: Dec. 28, 2007

(65) Prior Publication Data

US 2008/0213814 A1 Sep. 4, 2008

Related U.S. Application Data

(60) Provisional application No. 60/878,617, filed on Jan. 3, 2007.

(51) Int. Cl.
*G01N 33/553* (2006.01)
*G01N 33/573* (2006.01)

(52) U.S. Cl.
USPC ............ 435/7.4; 436/525; 436/526; 436/527; 436/531; 436/164; 436/805

(58) Field of Classification Search ................ None
See application file for complete search history.

(56) References Cited

U.S. PATENT DOCUMENTS

| | | | |
|---|---|---|---|
| 5,304,465 A | 4/1994 | Garland et al. | |
| 6,331,276 B1 * | 12/2001 | Takei et al. | 422/82.09 |
| 7,186,383 B2 | 3/2007 | Webster et al. | |
| 7,223,363 B2 | 5/2007 | McNeely et al. | |
| 7,511,820 B2 * | 3/2009 | Chau et al. | 356/445 |
| 2001/0053251 A1 | 12/2001 | Ikeda et al. | |
| 2004/0023415 A1 | 2/2004 | Sokolov et al. | |
| 2007/0109544 A1 | 5/2007 | Chau et al. | |
| 2007/0109545 A1 * | 5/2007 | Chau et al. | 356/445 |
| 2007/0117151 A1 | 5/2007 | Frederix et al. | |
| 2007/0134805 A1 | 6/2007 | Gilbert | |
| 2007/0134815 A1 * | 6/2007 | Chamberlin et al. | 436/525 |
| 2008/0044148 A1 * | 2/2008 | Robinson et al. | 385/122 |
| 2010/0178713 A1 * | 7/2010 | Nishiuma et al. | 436/525 |

FOREIGN PATENT DOCUMENTS

| WO | WO 90/11525 | 10/1990 |
|---|---|---|
| WO | WO 2006/073421 | 7/2006 |

OTHER PUBLICATIONS

Zhao et al, "Resonance Surface Plasmon Spectroscopy: Low Molecular Weight Substrate Binding to Cytochrome P450", Journal of the American Chemical Society, 2006, 128, 11004-11005.*

Lin et al, "Determination of organophosphorous pesticides by a novel biosensor based on localized surface plasmon resonance", Biosensors and Bioelectronics, 2006, 22, 513-518.*

International Search Report dated Oct. 1, 2008, issued in International Patent Application No. PCT/US08/50034, filed Jan. 2, 2008.

(Continued)

*Primary Examiner* — Chris L Chin
(74) *Attorney, Agent, or Firm* — Kilpatrick Townsend & Stockton LLP.

(57) ABSTRACT

The present invention provides a method of detecting changes in the refractive index at the surface of a localized surface plasmon resonance (LSPR) detection system. The method includes generating an insoluble product from an enzymatic substrate using an immobilized enzyme, wherein the insoluble product accumulates at a LSPR supporting surface. The method also includes detecting changes in the reflected or transmitted light of the surface arising from the presence of the insoluble product using LSPR.

16 Claims, 4 Drawing Sheets

OTHER PUBLICATIONS

Endo et al., "Multiple label-free detection of antigen-antibody reaction using localized surface plasmon resonance-based core-shell structured nanoparticle layer nanochip," 2006, Anal. Chem., 78(18), pp. 6465-6475.

Kim et al., "Enhanced sensitivity of surface plasmon resonance (SPR) immunoassays using a peroxidase-catalyzed precipitation reaction and its application to a protein microarray," 2005, Journal of Immunological Methods, 297, pp. 125-132.

Stuart et al., "Biological Applications of Localised Surface Plasmonic Phenomenae," 2005, IEE Proc. Nanobiotechnol, 152(1), pp. 13-32.

Takei et al., "Biological sensor based on localized surface plasmon associated with surface-bound Au/polystyrene composite microparticles," 1998, SPIE, 3515, pp. 278-283.

* cited by examiner

SEM photo of gold particles coated with the product of the enzymatic reaction (2)

Time (sec)

(3) transparent porous support (4)
magnetic bead magnet

ENZYMATIC ASSAY FOR LSPR

CROSS-REFERENCES TO RELATED APPLICATIONS

This application claims the benefit of U.S. Provisional Application No. 60/878,617, filed Jan. 3, 2007, incorporated in its entirety herein.

BACKGROUND OF THE INVENTION

The colorimetric assay based on an enzyme reaction for signal amplification has seen wide use in the field of clinical diagnostics because it is convenient to use and has sufficient sensitivities. The sensitivity is dictated by the turn over rate of the enzyme label, the enzymatic substrates used and the amount of the enzyme. Alkaline phosphatase and horseradish peroxidase are two of the most popular enzyme labels. The former is often used in conjunction with nitro-blue tetrazolium chloride (NBT) and/or 5-bromo-4-chloro-3'-indolylphosphate p-toluidine salt (BCIP). The latter is often used in conjunction with 3,3',5,5'-tetramethyl benzidine (TMB), 4-chloro-1-naphthol (4-CN), 3,3'-diaminobenzidine tetrahydrochloride (DAB) etc. Upon reaction of the enzymatic substrate with the enzyme, insoluble colored products precipitate. The insoluble product is detected visually for qualitative results, or with a simple optical detector for semi-quantitative results. Thus, how much insoluble product accumulates and how much optical density changes with accumulation dictates the detection limit.

Much effort has already gone into increasing the efficiency of the enzyme action and developing a substrate with an optically dense reaction product. There is not much room left for accelerating the enzymatic reaction by raising the temperature because higher temperatures lead to degradation of the enzyme. Increasing the amount of the enzyme does help, but there is a limit on how much antibody can be attached to a solid surface. This limit has already been reached with a porous membrane used for immuno-chromatographic kit; no drastic improvement can be expected. Another shortcoming associated with the colorimetric method is a poor dynamic range. As long as the detection method relied on measurement of absorbance, an accurate measurement is possible for optical densities below 2, and the minimum absorbance on the other hand is on the order of 0.1. Thus, the range is only 20, covering only slightly over one order of magnitude.

While improvements will certainly be made, there has not been a general approach applicable to a wide range of enzyme/substrate combinations. The present invention surprisingly offers a general approach that does not depend on improvements on a particular enzyme or substrate.

BRIEF SUMMARY OF THE INVENTION

In one embodiment, the present invention provides a method of detecting changes in the refractive index at the surface of a localized surface plasmon resonance (LSPR) detection system. The method includes generating an insoluble product from an enzymatic substrate using an immobilized enzyme, wherein the insoluble product accumulates at a LSPR supporting surface. The method also includes detecting changes in the reflected or transmitted light of the surface arising from the presence of the insoluble product using LSPR.

In a second embodiment, the present invention provides an LSPR sensor having a first solid support, an LSPR supporting surface disposed on the first solid support, an immobilized enzyme in close proximity to the LSPR supporting surface and an enzymatic substrate.

DETAILED DESCRIPTION OF THE INVENTION

I. General

The present invention provides a method of detecting an analyte via the use of a localized surface plasmon resonance (LSPR) supporting surface. The LSPR supporting surface includes a gold coated surface on which there is an array of gold coated nanoparticles such as beads. The method of the present invention detects the analyte using a sandwich assay. The method of the present invention detects the analyte by capturing the analyte with a first capture moiety immobilized on the gold surface of the beads of the LSPR supporting surface. The presence of the analyte is then detected using a second capture moiety having a detection moiety.

In a preferred embodiment, the sandwich assay is an immunoassay where the capture moieties are antibodies and the analyte is an antigen. In another preferred embodiment, the detection moiety is an enzyme, such that when the second capture moiety binds to the analyte, a soluble enzymatic substrate is introduced into the mixture such that the enzyme converts the enzymatic substrate to an insoluble product which accumulates on the LSPR supporting surface. The accumulation of the insoluble product on the LSPR supporting surface results in a shift in the wavelength of the reflected or transmitted light that is visible by the naked eye. It is the nature of LSPR that very little insoluble product is required to induce the wavelength shift visible to the naked eye. In contrast to the method of the present invention, existing methods detect the presence of the insoluble product directly using calorimetric methods, and thus require the deposition of large amounts of the insoluble product.

The method of the present invention increases the sensitivity for colorimetric enzyme immunoassay by making the insoluble product accumulate on the LSPR supporting surface. This results in enhanced detection by localized surface plasmon resonance effect, shortens the assay time by agitating the sample in a low volume reaction region and extends the dynamic range beyond a few orders of magnitude.

The sensitivity for calorimetric enzyme immunoassays can be enhanced by exploiting near-field optics associated with an LSPR supporting surface. In conventional assays, formation of the colored product from the enzymatic reaction is detected either visually, or by a simple device for monitoring absorption at a specific wavelength. If the colorimetric enzyme immunoassay takes place on an LSPR supporting surface, the production of the colored product can be detected indirectly at much lower concentrations by detecting the shift in the wavelength of the reflected or transmitted light. Nanoparticles adsorbed on a solid surface create an LSPR supporting surface that is characterized by a sharp extinction spectrum. The sharp extinction spectrum can be in any part of the electromagnetic spectrum, such as in the visible region. The sharp extinction spectrum is due to a localized surface plasmon phenomenon, i.e. a collective oscillatory motion of localized free electrons. The extinction spectrum exhibits a very sensitive dependence on the local refractive index. By monitoring refractive index change induced by accumulation of insoluble product on the LSPR supporting surface via its absorption spectrum, it is possible to detect the antigen at lower concentrations.

The conventional colorimetric method that relies on a straightforward optical detection of accumulated enzymatic reaction product has a dynamic range only slightly over one order of magnitude. This has been limited by the ability of most optical systems to measure optical density within the range of 0.1 to 1.5 with great accuracy. The method of the present invention can monitor the change in the extinction spectrum of the LSPR supporting surface at different wavelengths. While similar approaches have been tried with the conventional colorimetric assay, the conventional methods use direct monitoring of the colored product rather than indirect monitoring as practiced in the present invention. In addition, the sensitivity of the LSPR supporting surface can be tuned by manipulating physical parameters. Accordingly, the dynamic range can be expanded over several orders of magnitude.

II. Definitions

As used herein, the term "LSPR supporting surface" refers to a surface that enables the formation of an optical near-field through resonance oscillations of confined free electrons, commonly named a localized surface plasmon resonance. The LSPR supporting surface is characterized by nanoparticles, as described in greater detail below. The LSPR supporting surface can be opaque or transparent, and can transmit or reflect light, or both.

As used herein, the term "nanoparticles" refers to particles and beads having dimensions of between about $10^{-9}$ to about $10^{-7}$ meters. Nanoparticles can be made of any suitable material and include, but are not limited to, beads, pyramids, wires, mesh, etc. One of skill in the art will appreciate that other nanoparticles are useful in the present invention.

As used herein, the term "transition metal" refers to elements of the periodic table including Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au and Ac. One of skill in the art will appreciate that the transition metals described above can each adopt several different oxidation states, all of which are useful in the present invention. In some instances, the most stable oxidation state is formed, but other oxidation states are useful in the present invention.

As used herein, the term "solid support" refers any material on which a LSPR supporting surface can be added or grown. Examples of suitable solid supports include, but are not limited to, glass (including controlled-pore glass), polymers (e.g., polystyrene, polyurethane, polystyrene-divinylbenzene copolymer), silicone rubber, quartz, latex, a transition metal, magnetic materials, silicon dioxide, silicon nitride, gallium arsenide, and derivatives thereof. Except for the reactive sites on the surface, solid support materials are generally resistant to the variety of chemical reaction conditions to which they may be subjected. The solid support useful in the present invention can be smooth or roughened. A smooth surface is one having a minimum of features on the surface that lead to roughness. A roughened surface is one that has a multitude of features on the surface that create friction. The solid support of the present invention includes a first solid support and a second solid support. The solid support can be flat or non-flat, flexible or rigid. In addition, the solid support can be porous, mesh or fabric. The solid support can be opaque or transparent, and can transmit or reflect light, or both. One of skill in the art will appreciate that other solid supports are useful in the present invention.

As used herein, the term "LSPR detection system" refers to a system for detecting a target analyte by monitoring changes in the refractive index of an LSPR supporting surface. These changes can be either plasmon peak shifts, modification in the shape of the absorption, reflection or transmission spectrum or an associated metric such as the area or ratio of the absorption, reflection or transmission spectrum.

As used herein, the term "insoluble product" refers to the compound that accumulates on the LSPR supporting surface and alters the refractive index of the LSPR supporting surface. The insoluble product is formed by conversion of the enzymatic substrate by the enzyme. The insoluble product can be colored or colorless.

As used herein, the term "enzymatic substrate" refers to a soluble compound that is converted by the enzyme to the insoluble product that subsequently accumulates on and alters the refractive index of the LSPR supporting surface. Examples of compounds useful as the enzymatic substrate in the present invention are described below. The enzymatic substrate can be colored or colorless.

As used herein, the term "immobilized enzyme" refers to an enzyme that is immobilized on a solid support and is in close proximity to the LSPR supporting surface, and that converts the enzymatic substrate to the insoluble product. Examples of immobilized enzymes and methods for immobilizing the enzyme are described below.

As used herein, the term "immunoassay" refers to an assay to detect an analyte using two capture agents where one capture agent is typically bound to a solid support material and the second capture agent includes a detection moiety. A variety of immunoassay formats can be used, such as solid-phase ELISA immunoassays (see, e.g., Harlow & Lane, Antibodies, A Laboratory Manual (1988), for a description of immunoassay formats and conditions that can be used to determine specific immunoreactivity). Immunoassays which can be used to detect analytes include, for example, competitive and non-competitive assay systems such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. One of skill in the art will appreciate that other immunoassay are useful in the present invention.

As used herein, the term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the F(ab)'.sub.2 dimer into an Fab' monomer. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

As used herein, the term "sandwich assay" refers to assays in which the amount of captured analyte is directly measured. In one "sandwich" assay, for example, the capture agent can be bound directly to a solid substrate where it is immobilized. These immobilized capture agents then capture the target analyte present in the test sample. The target analyte thus immobilized is then bound by a second capture agent having a detection moiety thereon, such as a second agent bearing an enzyme. Alternatively, the detection moiety can be a labeled third agent specific to agents of the species from which the second agent is derived. The second agent can be modified with a detectable moiety, such as biotin, to which a third labeled molecule can specifically bind, such as enzyme-labeled streptavidin. The agents can be antibodies or adnectins, as described below.

As used herein, the term "transparent" refers to the ability of a material to transmit light. In the present invention, some solid support materials are transparent, absorbing little of the light passing through the material.

III. A Method of Detecting Changes in the Refractive Index at the Surface of a Localized Surface Plasmon Resonance (LSPR) Detection System The present invention provides a method of detecting changes in the refractive index at the surface of a localized surface plasmon resonance (LSPR) detection system. The method includes generating an insoluble product from an enzymatic substrate using an immobilized enzyme, wherein the insoluble product accumulates at a LSPR supporting surface. The method also includes detecting changes in the reflected or transmitted light of the surface arising from the presence of the insoluble product using LSPR, using the changes in the spectrum of light reflected by or transmitted through the LSPR surface.

The basic principle of the present invention is based on an enhancement effect due to localized surface plasmon associated with nano-scale noble metal particles. In these particles whose dimension is in the range from 5 nm up to a 1000 nm, there is a pronounced optical extinction due to resonance oscillations of confined free electrons. Resonating electrons produce strong localized electromagnetic fields with an intensity enhanced by a few orders of magnitude as compared to surface plasmons that are not localized. The localized field, commonly called optical near-field, extends a few tens of nm from the surface. When the refractive index changes within the near-field, the extinction by the particle is modified very sensitively. Taking advantage of this sensitivity, the present invention provides a method for a colorimetric enzyme assay in the vicinity of the LSPR supporting surface. When the product is deposited on the LSPR supporting surface, the extinction spectrum changes sufficiently for even visual detection when the deposition thickness is under 10 nm. It is not the absorbance of the enzyme product that is monitored. Rather, it is the change in the extinction spectrum of the LSPR supporting surface that is sensitively affected by the presence of the product in the vicinity. The wavelength to be monitored can be selected on the basis of the required sensitivity; the wavelength region closer to the peak, 20 to 50 nm, is suitable for high sensitivity, and those further away are suitable for lower sensitivity. Thus, by monitoring at multiple wavelengths or the whole spectrum, it is possible to extend the dynamic range.

While there are many ways of forming surface-adsorbed particles, the method of the present invention utilizes an approach whereby a monolayer of monodisperse particles is first adsorbed on a noble metal surface grown on a solid support. The solid support can be any appropriate material, such as silicon, glass or a polymer. Another noble metal layer is deposited on top of the nanoparticle monolayer. By careful selection of the nanoparticle dimensions and the thickness of the noble metal layers, it is possible to create an LSPR supporting surface whose extinction peak can be matched to any wavelength across the entire range of light to be detected. For example, any wavelength in the visible spectrum can be matched in this manner. Moreover, the different nanoparticle dimensions of the LSPR supporting surface exhibit different sensitivities so that using multiple types and dimensions of particles can be useful for further expanding the dynamic range. The particles of the present invention include, but are not limited to, spheres, triangles or particles fabricated of noble metals and other substances, i.e., made of polymer, metal, metal-alloy, or non-metal composite, may be hollow or porous, or cored with a differing material, liquid or substance interior and have a diameter, length or mass of 5 nm to 100 um and which can be patterned by mechanical, vacuum or chemical methods or created using and or removing of masks.

A. LSPR Supporting Surface

The LSPR supporting surface of the present invention enables detection of the change in the extinction spectrum of the LSPR supporting surface where the extinction spectrum is sensitive to the presence of a product. By monitoring changes in the refractive index induced by the presence of the insoluble product via absorption spectrum of the LSPR supporting surface, it is possible to detect the antigen at lower concentrations.

Figure 1:
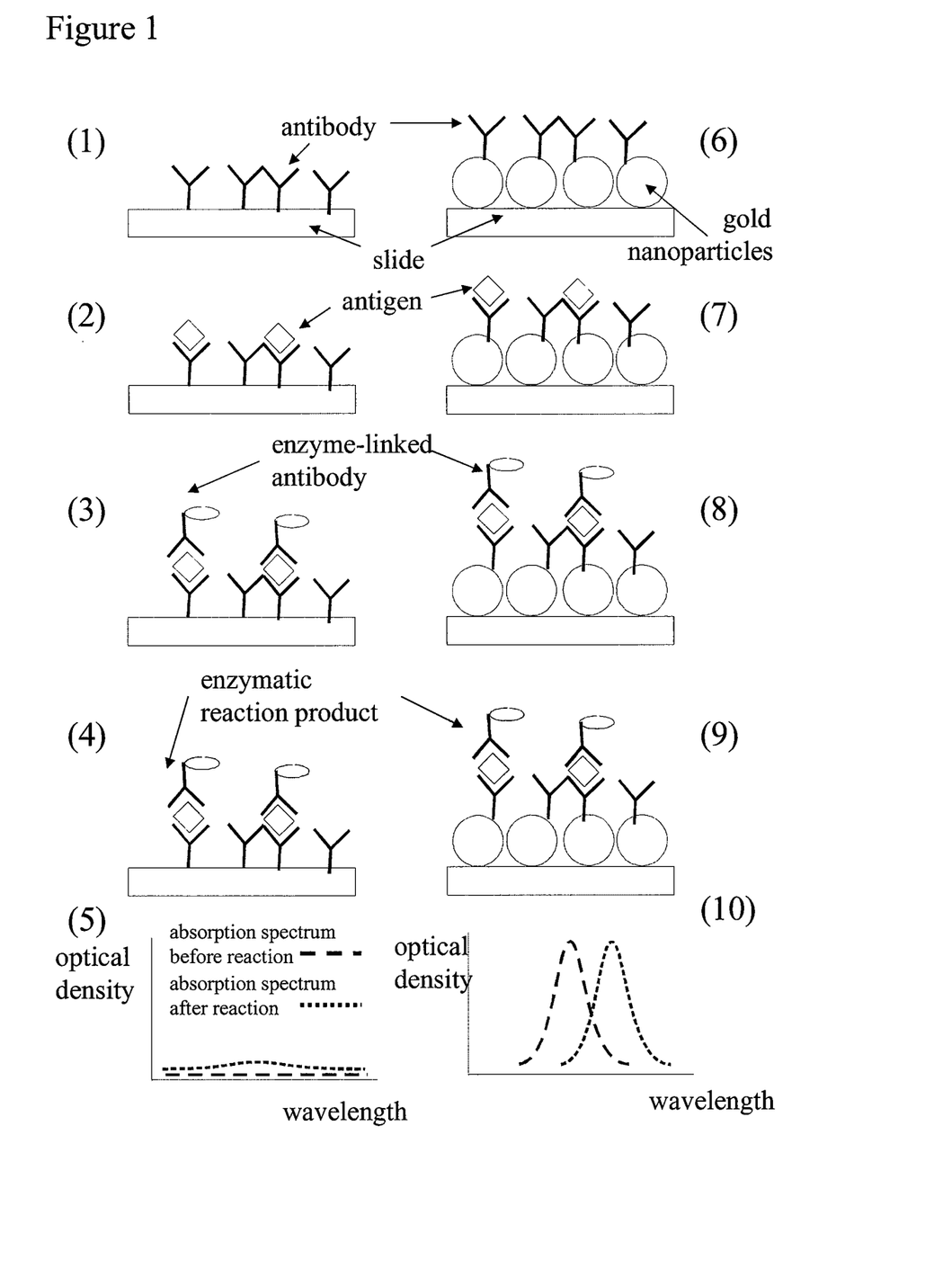
FIG. 1 shows a comparison of a colorimetric 2-step sandwich assay carried out in the conventional method and in the method of the present invention.

FIG. 1 describes a calorimetric 2-step sandwich assay carried out in the conventional method and in the method of the present invention. In the conventional case, the method starts with a surface coated with an antibody (1). Addition of a sample containing the target molecule (antigen) starts a binding event between the surface-bound antibody and the antigen (2). Then, an enzyme-linked secondary antibody is added (3). Addition of the substrate results in formation of a colored enzymatic reaction product (4). The amount of the antigen present in the sample is determined by how much colored product forms on the surface (5). In the method of the present invention, the method starts with a gold particle-coated surface with an immobilized antibody (6). The sample containing the antigen is added for the first antigen/antibody reaction (7). The secondary antibody is added (8), and the substrate is added for enzymatic reaction (9). Finally, the amount of the antigen is determined by the change in the extinction spectrum of the gold particle (10). The overall shift is toward longer wavelengths. Monitoring the spectrum shift at different wavelengths, or the whole spectrum, allows one to adjust the sensitivity.

Figure 2:
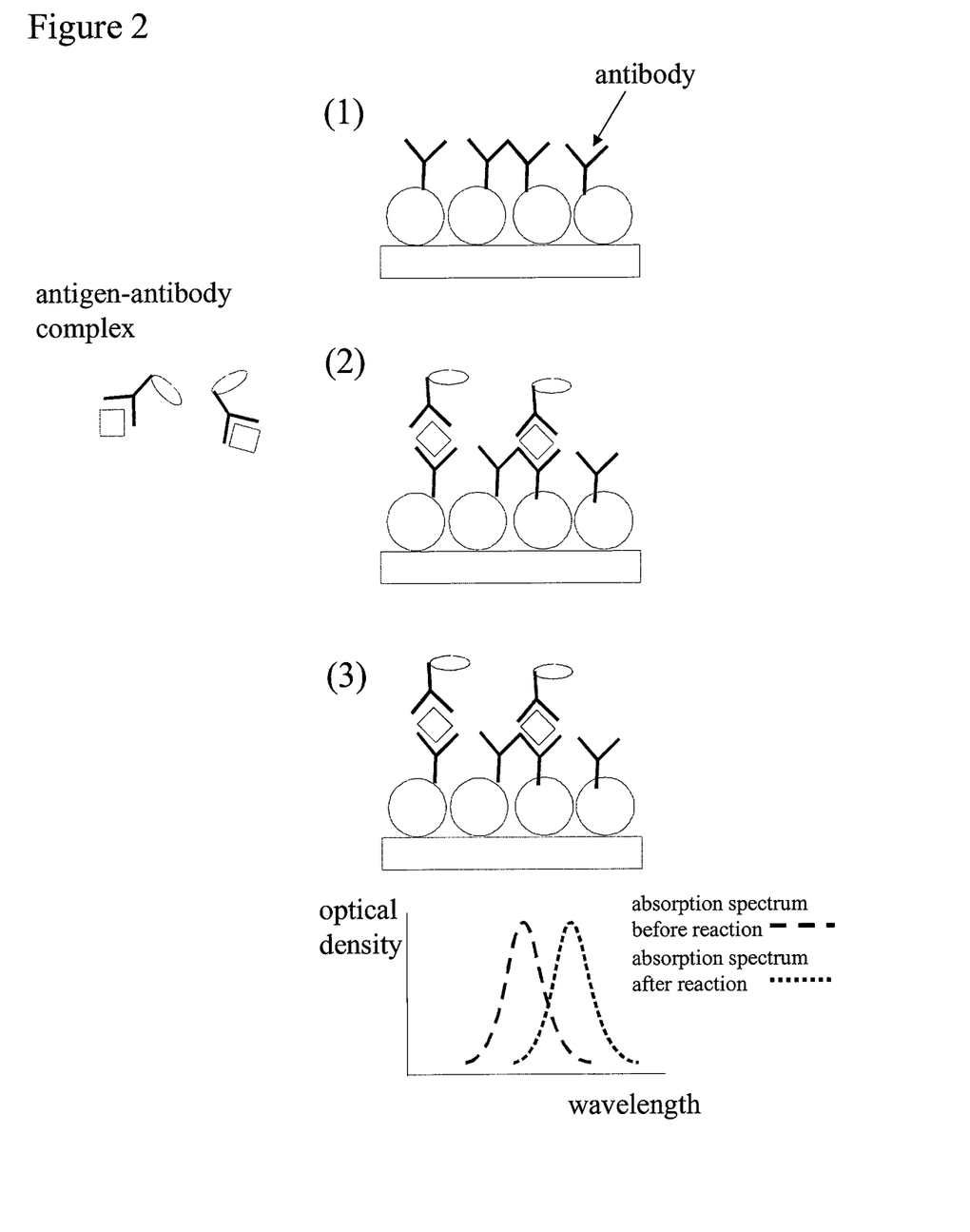
FIG. 2 shows a 1-step assay using the method of the present invention.

FIG. 2 shows how an alternative immunoassay mode called 1-step assay can be carried out. Here, the antigen/secondary antibody complex is allowed to form while both are still freely suspended in a liquid phase. The complex is captured by the surface-bound antibody (2). As with the 2-step assay in FIG. 1, detection is carried out by monitoring the change in the extinction spectrum of the gold particle (3). The 1-step assay is suitable for a test that demands a shorter assay time.

Figure 3:
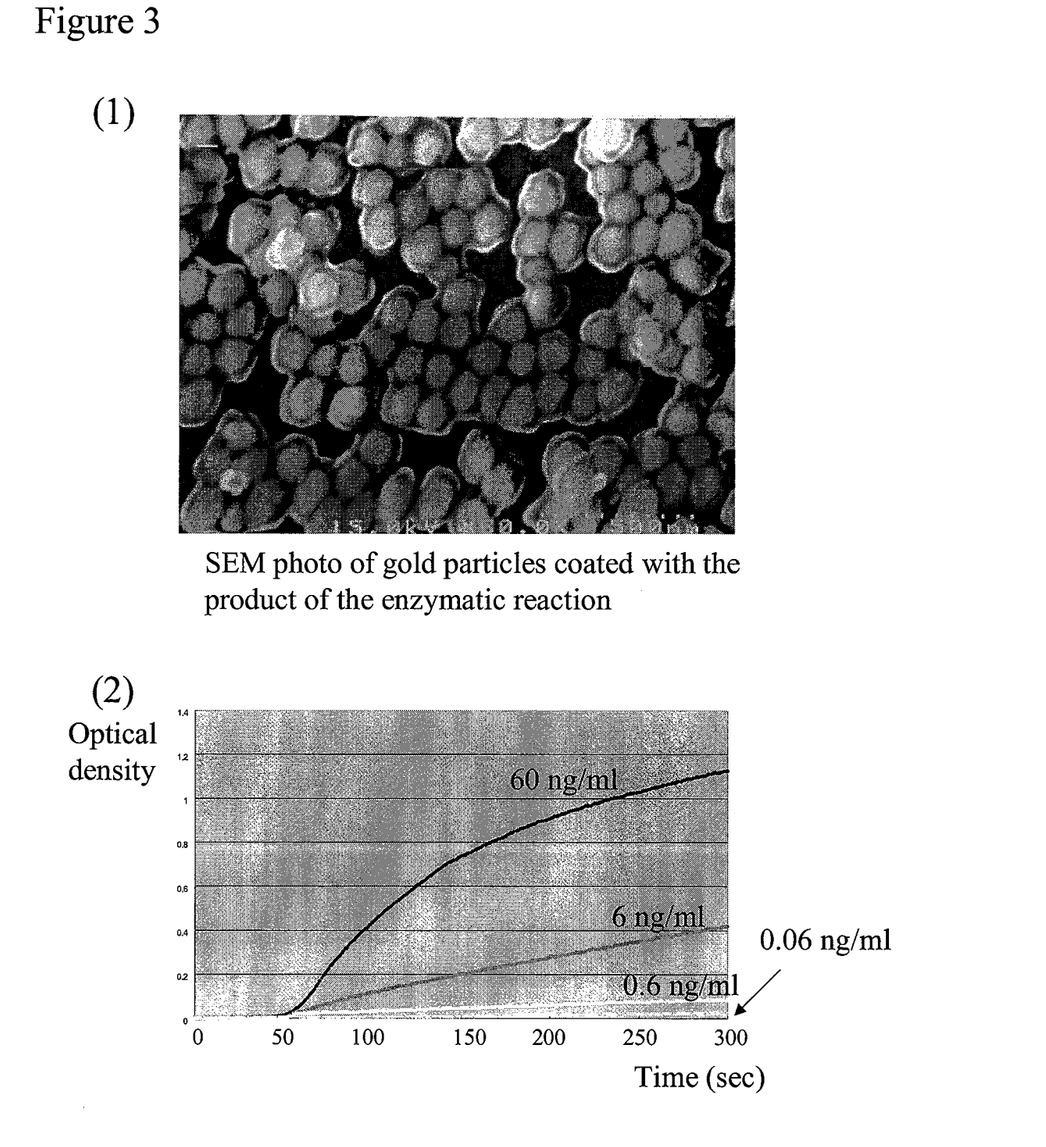
FIG. 3 shows a scanning electron microscope (SEM) photo of the gold nanoparticles after the enzymatic reaction has been carried out (1) and a graph showing changes in the optical density during the enzymatic reaction at the end of a IL-6 assay (2).

FIG. 3 (1) shows a scanning electron microscope (SEM) photo of the gold particle after the enzymatic reaction has been carried out; the label was alkaline phosphatase, and the substrate was a mixture of NBT and BCIP. The particle diameter is 100 nm, and the shell surrounding the particle is the deposited product of the enzymatic reaction. The deposition thickness is estimated to be about 20 nm. (2) is a graph showing changes in the maximum position of the optical density during the enzymatic reaction at the end of a IL-6 assay. The peak of the extinction spectrum of the gold particle was at 570 nm, and the wavelength range of monitoring was between 620 and 630 nm. The BCIP/NBT substrate mixture was injected at t=50 sec. The antigen concentration was 60, 6, 0.6, 0.06 ng/ml from top to bottom.

The LSPR supporting surface can include nanoparticles that can be arrayed, patterned or layered, or any combination thereof. The nanoparticles can be of any size and shape, such as colloids, mesh, nanorods, nanowire and beads. The nanoparticles can be a monolayer or a multilayer of nanoparticles. In some embodiments, the nanoparticles form a monolayer.

The nanoparticles of the LSPR supporting surface can be made of a single substance or a mixture of substances. When the nanoparticles are made from a mixture of substances, the mixture can be homogeneous or heterogeneous, such that 2 or more layers of material are formed in the nanoparticle. The nanoparticles can be hollow or porous. The nanoparticles can be opaque or transparent, and can transmit or reflect light, or both.

The nanoparticles of the LSPR supporting surface of the present invention can be made from any useful material. Examples of materials useful as the nanoparticles of the present invention include, but are not limited to, metals, polymers, ceramics (such as silica) and glasses.

In some embodiments, the nanoparticles of the present invention comprise a transition metal that include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au and Ac. One of skill in the art will appreciate that the transition metals described above can each adopt several different oxidation states, all of which are useful in the present invention. In some instances, the most stable oxidation state is formed, but other oxidation states are useful in the present invention. In addition, the transition metals of the present invention can be metal oxides. In some embodiments, the transition metal can be Au, Ag, Ta, Pt, Pd, Cu or Rh. In other embodiments, the transition metal can be gold.

Polymers useful as the nanoparticles of the LSPR supporting surface of the present invention can be any suitable polymer. In some embodiments, the polymer can be polystyrene, polymethacrylate or polyacrylate. In some embodiments, the nanoparticles can be glass or a polymer including polystyrene, polymethacrylate or polyacrylate. Ceramics useful as the nanoparticles of the present invention can be any ceramic. In some embodiments, the ceramics can be $SiO_2$ or glass.

In other embodiments, a mixture of materials are used for the nanoparticles of the LSPR supporting surface. Any combination of materials can be used. In some embodiments, the nanoparticles can be polystyrene coated with gold or glass coated with gold. One of skill in the art will appreciate that other materials are useful as the nanoparticles of the present invention.

In another embodiment, each nanoparticle of the LSPR supporting surface is a bead having a top portion and a bottom portion, wherein the top portion is coated with the transition metal. In other embodiments, the nanoparticle bead is polystyrene and the transition metal is gold. When the nanoparticle beads of the present invention are coated, such as gold coating a glass bead, the coating can be of any useful thickness. In some embodiments, the gold coating can be 1 nm or less, several nanometers, or hundreds of nanometers in thickness. Coating of the nanoparticles can be accomplished using techniques known to one of skill in the art, such as evaporation, sputtering and CVD.

The nanoparticles of the LSPR supporting surface of the present invention can be of any size and dimensions. In some embodiments, the nanoparticles are from 5 nm to about 1000 nm in size. In some other embodiments, the beads have a diameter from about 10 nm to about 1000 nm. In still other embodiments, the beads have a diameter from about 50 nm to about 500 nm. One of skill in the art will appreciate that nanoparticles of other sizes and dimensions are useful in the present invention.

The size and shape of the nanoparticles of the LSPR supporting surface used in the present invention allows the extinction peak of the LSPR supporting surface to be tuned so as to match any wavelength, such as across the entire range of visible light. The dynamic range and sensitivity of the LSPR supporting surface can also be tuned using different shapes, sizes and materials for the nanoparticles.

The solid support of the present invention can be any material that supports the LSPR supporting surface. Materials useful for the solid support include, but are not limited to, transition metals, ceramics, polymers and glass. One of skill in the art will appreciate that other materials are useful in the present invention.

The surface of the solid support can be modified such as by smoothing the surface or by roughening the surface so as to make nanoscale features. In some embodiments, the solid support is coated with a transition metal, such as those described above. In some other embodiments, the solid support is coated with gold. The coating can be of any useful thickness, from less than 1 nm, including several nanometers and up to hundreds of nanometers.

The LSPR supporting surface and the solid support material can be opaque or transparent at the wavelength of light used to detect changes in the refractive index of the LSPR supporting surface. In some embodiments, the reflected light is used to detect changes in the refractive index of the LSPR supporting surface. In other embodiments, the transmitted light is used to detect changes in the refractive index of the LSPR supporting surface. In some other embodiments, both the reflected light and the transmitted light are used to detect the presence of the insoluble product.

B. Assay, Enzymes and Enzymatic Substrates

The method of the present invention can be practiced in any suitable assay where an analyte is captured by a capture moiety and then detected using a detection moiety. Typically, it is a sandwich assay involving a capture agent and a detecting agent. Most commonly, the agents are antibodies, but they can be hormone receptors, adnectins or any other combination of analyte binding agents.

In some embodiments, the assay is an immunoassay. A variety of immunoassay formats can be used include, but are not limited to, solid-phase ELISA immunoassays (see, e.g., Harlow & Lane, Antibodies, A Laboratory Manual (1988), for a description of immunoassay formats and conditions that can be used to determine specific immunoreactivity). Immunoassays which can be used to detect analytes include, for example, competitive and non-competitive assay systems such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. In a preferred embodiment, the assay is a sandwich assay such as an ELISA assay. The ELISA assay involves affixing an unknown amount of antigen to a surface, and then washing a specific antibody over the surface so that it can bind the antigen. This antibody links to an enzyme, and in the final step a substance is added that the enzyme can convert to some detectable signal. Thus, in the case of fluorescence ELISA, when light is shined on the sample, any antigen/antibody complexes will fluoresce so that the amount of antigen in the sample can be measured.

Performing an ELISA involves at least one antibody with specificity for a particular antigen. The sample with an unknown amount of antigen is immobilized on a solid support either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample.

Enzymes useful in the present invention are those that convert a soluble compound into an insoluble compound. Examples of enzymes useful in the present invention include, but are not limited to, alkaline phosphatase and horseradish peroxidase. One of skill in the art will appreciate that other enzymes are useful in the present invention.

Enzymatic substrates useful in the present invention include those that are converted by an enzyme from a soluble compound to an insoluble compound. In some embodiments, the soluble compound has no color and the insoluble compound is colored. Examples of enzymatic substrates include, but are not limited to, nitro-blue tetrazolium chloride (NBT), 5-bromo-4-chloro-3'-indolylphosphate p-toluidine salt (BCIP), 3,3',5,5'-tetramethyl benzidine (TMB), 4-chloro-1-naphthol (4-CN) and 3,3'-diaminobenzidine tetrahydrochloride (DAB). Additional enzymatic substrates include Electro-ChemiLuminescent chemicals known as ECL and ECL Plus. One of skill in the art will appreciate that other enzymatic substrates are useful in the present invention.

In other embodiments, the enzyme is immobilized by attachment to an antibody. In some other embodiments, the enzyme is immobilized via a sandwich assay.

A number of different ways are available for positioning the capture agent. The most straightforward method places the agent directly on the surface of the LSPR supporting surface. It is also possible to attach the capture agent on a surface distinct from the gold particle. This surface is fixed in position relative to the gold particle permanently, or just during the duration of the enzyme reaction. For example, a capture agent can be immobilized on the solid support, or on a second solid support such as a magnetic bead. In some embodiments, the capture agent is an antibody.

Figure 4:
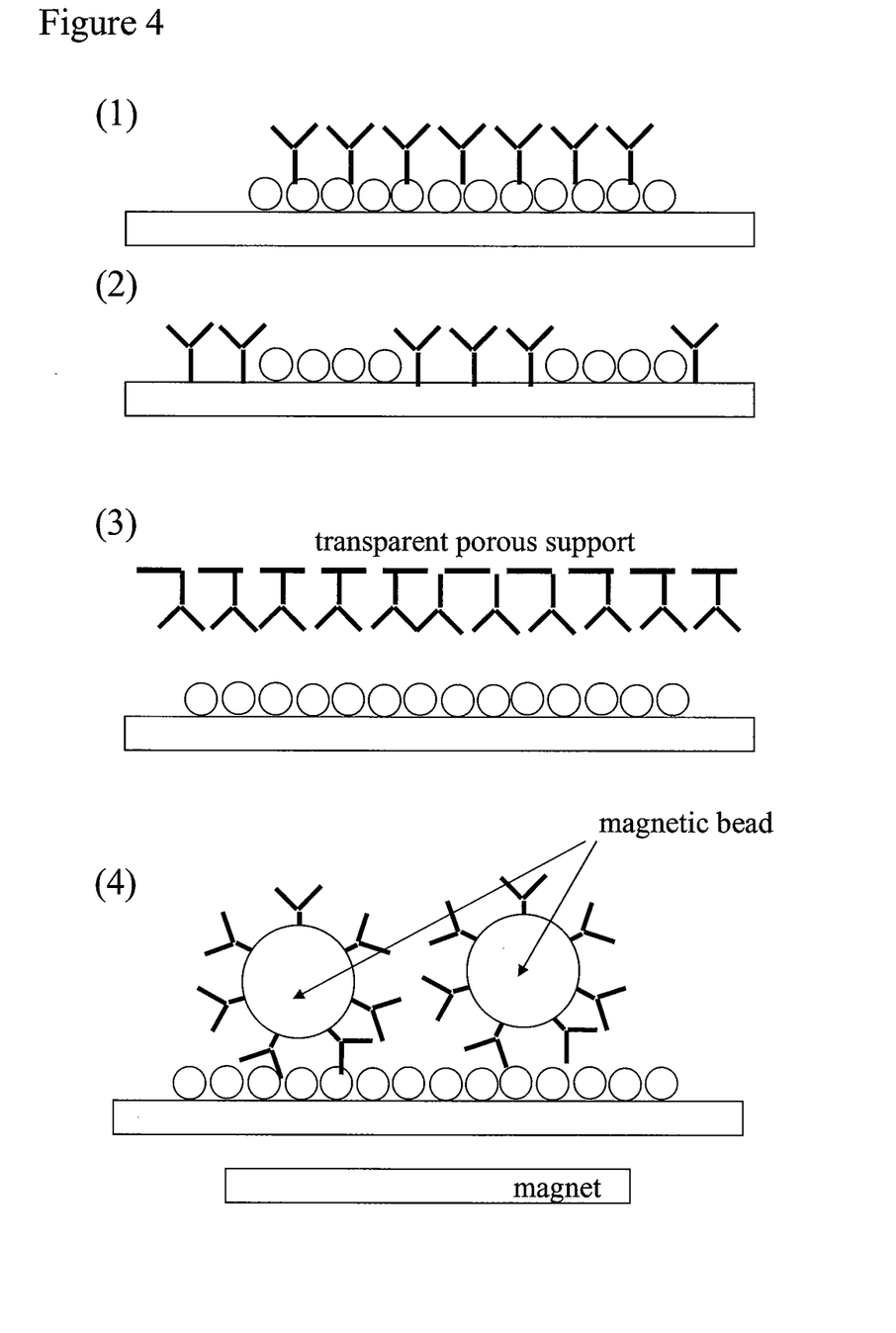
FIG. 4 shows a variety of ways in which the antibody can be attached either to the nanoparticles (1), to a first solid support (2) and to a second solid support (3,4).

The enzyme of the present invention can be immobilized to a nanoparticle or solid support in any suitable fashion. Immobilization of the enzyme can be through covalent bond formation, ionic bond formation, hydrogen bonding and van der Waals forces, among others. FIG. 4 depicts various ways in which the antibody can be attached. The antibody can be attached directly on top of the nanoparticles of the LSPR supporting surface as in (1) or on separate regions in close vicinity to the nanoparticles (2). Alternatively the antibody can be attached on a separate surface that can be placed in the close vicinity of the antibody-coated surface; here the supporting surface is made porous as well as transparent in order to assure access of the antigen to the antibody and to allow the interrogating light to reach the antibody-coated surface. Another approach utilizes antibody-coated magnetic beads that can be brought in contact with the gold particle coated surface by an external magnet (4). After deposition of the enzymatic reaction product, the magnetic beads can be removed to facilitate the optical reading. The advantage of attaching the antibody on a separate surface is to increase the signal; when the enzymatic reaction product deposits on the bare LSPR supporting surface rather than those already covered by an antibody, the change becomes greater.

In another embodiment, the LSPR supporting surface is on a first solid support. In other embodiments, the enzyme is immobilized on the first solid support. In some other embodiments, the enzyme is immobilized on a second solid support, wherein the second solid support is in close proximity to the LSPR supporting surface during the generating step. In still other embodiments, the second solid support is transparent. In yet other embodiments, the second solid support is a magnetic bead. In another embodiment, the surface of the first solid support is smooth. In yet another embodiment, the surface of the first solid support is roughened.

Magnetic beads or particles, such as magnetic latex beads and iron oxide particles, that are useful in the claimed invention are known to those of skill in the art. For example, magnetic particles are described in U.S. Pat. No. 4,672,040. Magnetic particles are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.).

Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (*Proc. Natl. Acad. Sci. U.S.A.* 92(14):6552-6556 (1995)) discloses an alternative to antibodies based on cytochrome $b_{562}$. Ku et al. (1995) generated a library in which two of the loops of cytochrome $b_{562}$ were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins may be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96(5):1898-1903 (1999)) discloses an antibody mimic based on a lipocalin scaffold (Anticalin®). Lipocalins are composed of a barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies.

Anticalins® are small, single chain peptides, typically between 160 and 180 residues, which provides several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49(2):209-216 (2003)) discusses a methodology for reducing antibodies into smaller peptidomimetics, they term "antibody like binding peptidomemetics" (ABiP) which may also be useful as an alternative to antibodies.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics).

Additional methods for linking the enzyme to the surface include the use of homobifunctional and heterobifunctional linkers. Zero-length cross linking reagents induce the direct conjugation of two ligands without the introduction of any extrinsic material. Agents that catalyze the formation of disulfide bonds belong in this category. Another example is reagents that induce the condensation of carboxy and primary amino groups to form an amide bond, such as carbodiimides, ethylchloroformate, Woodward's reagent K1, carbonyldiimidazole, etc. Homobifunctional reagents carry two identical functional groups, whereas heterobifunctional reagents contain two dissimilar functional groups. A vast majority of the heterobifunctional cross-linking agents contains a primary amine-reactive group and a thiol-reactive group. A novel heterobifunctional linker for formyl to thiol coupling was disclosed by (Heindel, N. D. et al., Bioconjugate Chem. 2, 427-430 (1991)). In a preferred embodiment, the covalent cross-linking agents are selected from reagents capable of forming disulfide (—S—S—), glycol (—CH(OH)—CH(OH)—), azo (—N=N—), sulfone (—S(=O2)-), or ester (—C(=O)—O—) bridges.

In a different approach, the ligands are linked via their oligosaccharides. Chemical or enzymatic oxidation of oligosaccharides on polypeptide ligands to aldehydes yields unique functional groups on the molecule, which can react with compounds containing, for example, amines hydrazines, hydrazides, or semicarbazides. Since the glycosylations sites are well defined in polypeptide molecules, selective coupling via oxidized oligosaccharide moieties will yield in a more uniform product than other coupling methods, and is expected to have less adverse effect on the receptor binding properties of the ligands. Carbohydrate-directed heterobifunctional cross-linking agents are, for example, disclosed in copending patent application Ser. No. 07/926,077 filed 5 Aug. 1992, U.S. Pat. No. 5,329,029.

C. Detection

Detection of the color change in the method of the present invention can be by any detection method. In some embodiments, the detection method is by colorimetric detection using suitable devices. In other embodiments, the detection is by the naked eye. Detection of the change in refractive index for the LSPR supporting surface is performed at any wavelength, especially light having a wavelength of from about 200 to about 1000 nm. Detection instruments that are useful for detecting the change in refractive index of the LSPR supporting surface, include, but are not limited to, UV-Vis spectrometers and plate readers.

IV. LSPR Sensor

The LSPR sensor of the present invention includes a first solid support, an LSPR supporting surface as described above and disposed on the first solid support, an immobilized enzyme in close proximity to the LSPR supporting surface and an enzymatic substrate.

V. Kits

In some embodiments, the present invention provides a kit having an LSPR sensor as described above, and an enzymatic substrate. The kits of the present invention can also include solvents, buffers, stabilizers and instructions.

VI. Examples

Example 1

Detecting changes in Refractive Index at an LSPR Surface

The protocol for an immunoassay on a LSPR surface proceeds according to various steps that are described here after.
Step 1. Immobilization of the Capturing Antibody:
An LSPR supporting surface was first prepared using methods known in the art, including depositing gold on a glass substrate, followed by forming a monolayer of polystyrene beads on the gold coated glass substrate, and then depositing another layer of gold across the whole surface. The gold coated surface is then modified with a self-assembled monolayer (SAM) having a mixture of hydroxyl-alkanethiol and carboxyl-alkanethiol in a 9:1 ratio.

The SAM-functionalized LSPR supporting surface was washed with 0.05% Tween20 in water. It was then rinsed with $ddH_2O$ and dried. The carboxylic groups of the LSPR supporting surface were activated with a solution of (100 mM NHS+400 mM EDC in 0.1 M MES buffer) for 15 to 30 minutes, as described in, i.e., Greg T. Hermanson, *Bioconjugate Techniques*, Academic Press, San Diego, 1996.

After 30 minutes of incubation, the solution was rinsed away and replaced with a solution of 500 nM of antibody solution. The antibody solution was in an amine-free buffer, such as PBS. Antibody immobilization was performed for 30 minutes up to 24 hrs. For example, a capturing antibody for C-reactive protein detection is the mouse monoclonal anti-CRP antibody from Biodesign, Cat# M86007M. The remaining EDC/NHS-activated carboxylic groups were quenched by reacting the surface for 30 minutes with a solution of 50 mM amino-Polyethylene oxide in water.

The surface was then rinsed with water and further blocked against non-specific binding by incubation in StartingBlock buffer from Pierce chemicals for 15 minutes. The LSPR supporting surface activated with the capturing antibody was then rinsed with $ddH_2O$ and was kept in a humid environment until the sensor was used.
2. Capturing of Antigen:
C-reactive protein or CRP, was diluted in various concentrations from 1 pM ($10^{-12}$ M) up to 1 uM ($10^{-6}$ M) in a buffer (Buffer A) made of Phosphate Saline buffer (PBS), 1 mM $Ca^{2+}$, 0.01% v/v Tween20 and 10 uM BSA (Bovine Serum Albumin). Then the antigen was incubated with the antibody activated LSPR supporting surface for a time period ranging from 5 minutes to 2 hrs.
3. Second Anti-Antigen Antibody Capture:
The sensor was then incubated with polyclonal goat anti-human CRP antibody (Bethyl Labs, Cat# A80-125A) at concentrations of 250 nM in buffer A. This antibody can labeled with an enzyme or a probe (e.g. biotin). After 15 to 30 minutes of incubation, the second antibody was rinsed away with buffer.
4. Enzyme-Linked Antibody Against the Second Anti-Antigen Antibody:
The enzyme-linked antibody, a donkey anti goat IgG antibody alkaline phosphatase conjugate from Bethyl Lab, Cat# A50-101AP, was then reacted for about 2 to 30 minutes and then rinsed away with Buffer A.
5. Colorimetric Development:
An enzymatic substrate was added to the LSPR supporting surface and incubated for 30 seconds to 10 minutes. The unreacted enzymatic substrate was rinsed away with water. The absorption spectrum or reflection spectrum of the surface was then measured.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of detecting changes in the refractive index at the surface of a localized surface plasmon resonance (LSPR) detection system, the method comprising:
   a) generating an insoluble product from an enzymatic substrate using an immobilized enzyme, wherein the insoluble product accumulates on a LSPR supporting surface, and the enzyme is immobilized by attachment to an antibody; and
   b) detecting changes in the refractive index via the reflected or transmitted light of the surface arising from the presence of the insoluble product using LSPR,
   wherein the surface comprises nanoparticles, wherein each nanoparticle is from about 5 nm to about 1000 nm in size, and each nanoparticle comprises a transition metal selected from the group consisting of Au, Ag, Ta, Pt, Pd, Rh and Cu, and glass or a polymer selected from the group consisting of polystyrene, polymethacrylate and polyacrylate.

2. The method of claim 1, wherein the transition metal is gold.

3. The method of claim 1, wherein the nanoparticle is a bead having a top portion and a bottom portion, wherein the top portion is coated with the metal.

4. The method of claim 3, wherein the nanoparticle bead comprises polystyrene and the metal comprises gold.

5. The method of claim 1, wherein the enzymatic substrate is a member selected from the group consisting of nitro-blue tetrazolium chloride (NBT), 5-bromo-4-chloro-3'-indolylphosphate p-toluidine salt (BCIP), 3,3',5,5'-tetramethyl benzidine (TMB), 4-chloro-1-naphthol (4-CN) and 3,3'-diaminobenzidine tetrahydrochloride (DAB).

6. The method of claim 1, wherein the enzyme is a member selected from the group consisting of alkaline phosphatase and horseradish peroxidase.

7. The method of claim 1, wherein the enzyme is immobilized via a sandwich assay.

8. The method of claim 1, wherein the detecting step involves detecting changes in the reflected light of the surface arising from the presence of the insoluble product using LSPR.

9. The method of claim 1, wherein the detecting step involves detecting changes in the transmitted light of the surface arising from the presence of the insoluble product using LSPR.

10. The method of claim 1, wherein the LSPR supporting surface is on a first solid support.

11. The method of claim 10, wherein the enzyme is immobilized on the first solid support.

12. The method of claim 10, wherein the enzyme is immobilized on a second solid support.

13. The method of claim 12, wherein the second solid support is transparent.

14. The method of claim 12, wherein the second solid support is a magnetic bead.

15. The method of claim 10, wherein the surface of the first solid support is smooth.

16. The method of claim 10, wherein the surface of the first solid support is roughened.

* * * * *